(12) United States Patent
Yadin et al.

(10) Patent No.: US 8,298,280 B2
(45) Date of Patent: Oct. 30, 2012

(54) STENT WITH PROTRUDING BRANCH PORTION FOR BIFURCATED VESSELS

(75) Inventors: Amnon Yadin, Pleasanton, CA (US); Daryush Mirzaee, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2668 days.

(21) Appl. No.: 11/010,730

(22) Filed: Dec. 14, 2004

(65) Prior Publication Data

US 2005/0102023 A1  May 12, 2005

Related U.S. Application Data

(63) Continuation-in-part of application No. 10/802,036, filed on Mar. 17, 2004, now Pat. No. 7,341,598, which is a continuation-in-part of application No. 10/705,247, filed on Nov. 12, 2003, now abandoned, which is a continuation-in-part of application No. 10/644,550, filed on Aug. 21, 2003, now Pat. No. 7,220,275.

(51) Int. Cl.
 *A61F 2/06* (2006.01)
(52) U.S. Cl. ..................... 623/1.35; 623/1.15
(58) Field of Classification Search ............... 623/1.15, 623/1.16, 1.35; 606/200
See application file for complete search history.

(56) References Cited

U.S. PATENT DOCUMENTS

| | | |
|---|---|---|
| 1,596,754 A | 8/1926 | Moschelle |
| 3,657,744 A | 4/1972 | Ersek |
| 3,872,893 A | 3/1975 | Roberts |
| 4,140,126 A | 2/1979 | Choudhury |
| 4,309,994 A | 1/1982 | Grunwald |
| 4,410,476 A | 10/1983 | Redding et al. |
| 4,413,989 A | 11/1983 | Schjeldahl |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,005 A | 9/1988 | Ginsburg et al. ............... 604/53 |

(Continued)

FOREIGN PATENT DOCUMENTS

CA  2220864  7/1999

(Continued)

OTHER PUBLICATIONS

U.S. Appl. No. 09/325,996, filed Jun. 4, 1999, Vardi et al.

(Continued)

*Primary Examiner* — Brian Pellegrino
(74) *Attorney, Agent, or Firm* — Vidas, Arrett & Steinkraus (57) ABSTRACT

The present invention is directed to a stent for use in a bifurcated body lumen having a main branch and a side branch. The stent comprises a radially expandable generally tubular stent body having proximal and distal opposing ends with a body wall having a surface extending therebetween. The stent also comprises a branch portion that is deployable outwardly from the stent body into a branch vessel.

19 Claims, 6 Drawing Sheets

U.S. PATENT DOCUMENTS

| | | |
|---|---|---|
| 4,769,029 A | 9/1988 | Patel |
| 4,774,949 A | 10/1988 | Fogarty ..................... 128/348.1 |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,905,667 A | 3/1990 | Foerster et al. ..................... 128/4 |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Cardon |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,487,730 A | 1/1996 | Marcadis et al. ................ 604/96 |
| 5,489,271 A | 2/1996 | Anderson |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,636,641 A | 6/1997 | Fariabi ......................... 600/585 |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,679,400 A | 10/1997 | Tuch |
| 5,683,450 A | 11/1997 | Goicoechea et al. ............. 623/1 |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,348 A | 1/1998 | Krogh ............................ 602/41 |
| 5,707,354 A | 1/1998 | Salmon |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,749,890 A | 5/1998 | Shaknovich ................... 606/198 |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,773 A | 5/1998 | Evans et al. ....................... 623/1 |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,800,450 A | 9/1998 | Lary et al. |

| Patent | Date | Name |
|---|---|---|
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,893,887 A | 4/1999 | Jayaraman ................. 623/1 |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,925,061 A * | 7/1999 | Ogi et al. ................. 623/1.2 |
| 5,928,248 A | 7/1999 | Acker |
| 5,938,682 A | 8/1999 | Hojeibane |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,017 A | 10/1999 | Berg et al. .................. 606/198 |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,093,203 A | 7/2000 | Uflacker ..................... 612/1.12 |
| 6,096,073 A | 8/2000 | Webster et al. |
| 6,099,497 A | 8/2000 | Adams et al. |
| 6,113,579 A | 9/2000 | Eidenschink et al. ......... 604/264 |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,143,002 A | 11/2000 | Vietmeier ..................... 606/108 |
| 6,152,945 A | 11/2000 | Bachinski et al. |
| 6,159,238 A | 12/2000 | Killion et al. ................. 612/1.11 |
| 6,165,195 A | 12/2000 | Wilson et al. |
| 6,165,197 A | 12/2000 | Yock |
| 6,165,214 A | 12/2000 | Lazarus |
| 6,168,621 B1 | 1/2001 | Vrba ............................. 623/1.2 |
| 6,179,867 B1 | 1/2001 | Cox |
| 6,183,506 B1 | 2/2001 | Penn et al. |
| 6,183,509 B1 | 2/2001 | Dibie |
| 6,187,033 B1 * | 2/2001 | Schmitt et al. ............... 623/1.35 |
| 6,190,403 B1 | 2/2001 | Fischell et al. |
| 6,193,746 B1 | 2/2001 | Strecker |
| 6,203,568 B1 | 3/2001 | Lombardi et al. ........... 623/1.13 |
| 6,203,569 B1 | 3/2001 | Wijay |
| 6,210,380 B1 | 4/2001 | Mauch |
| 6,210,429 B1 | 4/2001 | Vardi et al. |
| 6,210,433 B1 | 4/2001 | Larre ........................... 623/1.15 |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,254,593 B1 | 7/2001 | Wilson ......................... 606/1.11 |
| 6,258,073 B1 | 7/2001 | Mauch |
| 6,258,099 B1 | 7/2001 | Mareiro et al. |
| 6,258,115 B1 | 7/2001 | Dubrul ......................... 606/200 |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,316 B1 | 7/2001 | Shaolian et al. ............. 623/1.11 |
| 6,261,319 B1 | 7/2001 | Kveen et al. |
| 6,264,662 B1 | 7/2001 | Lauterjung ................... 606/108 |
| 6,264,682 B1 | 7/2001 | Wilson et al. |
| 6,264,686 B1 | 7/2001 | Rieu et al. .................... 623/1.16 |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,293,968 B1 | 9/2001 | Taheri .......................... 623/1.15 |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,822 B1 | 12/2001 | Chouinard ................... 623/1.35 |
| 6,325,826 B1 | 12/2001 | Vardi et al. |
| 6,334,864 B1 | 1/2002 | Amplatz et al. .............. 606/200 |
| 6,334,870 B1 | 1/2002 | Her et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,383,213 B2 | 5/2002 | Wilson et al. ................ 623/1.11 |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,508,836 B2 | 1/2003 | Wilson et al. ................ 623/1.35 |
| 6,511,504 B1 | 1/2003 | Lau et al. |
| 6,511,505 B2 | 1/2003 | Cox et al. |
| 6,517,558 B2 | 2/2003 | Gittings et al. ............... 606/153 |
| 6,520,988 B1 | 2/2003 | Colombo et al. |
| 6,527,799 B2 | 3/2003 | Shanley |

| Patent Number | Date | Inventor |
|---|---|---|
| 6,540,719 B2 | 4/2003 | Bigus et al. |
| 6,540,779 B2 | 4/2003 | Richter et al. |
| 6,572,647 B1 | 6/2003 | Supper |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. ............. 623/1.11 |
| 6,596,022 B2 | 7/2003 | Lau et al. |
| 6,599,316 B2 | 7/2003 | Vardi et al. |
| 6,645,241 B1 | 11/2003 | Strecker |
| 6,645,242 B1 | 11/2003 | Quinn ................. 623/1.16 |
| 6,689,156 B1 | 2/2004 | Davidson et al. |
| 6,692,483 B2 | 2/2004 | Vardi et al. |
| 6,695,877 B2 | 2/2004 | Brucker et al. ............ 623/1.16 |
| 6,706,062 B2 | 3/2004 | Vardi et al. |
| 6,749,628 B1 | 6/2004 | Callol et al. ............. 623/1.15 |
| 6,776,793 B2 | 8/2004 | Brown et al. ............ 623/1.15 |
| 6,811,566 B1 | 11/2004 | Penn et al. ............. 623/1.15 |
| 6,835,203 B1 | 12/2004 | Vardi et al. ............. 623/1.34 |
| 6,858,038 B2 | 2/2005 | Heuser ................. 623/1.35 |
| 6,884,258 B2 | 4/2005 | Vardi et al. ............. 623/1.11 |
| 6,896,699 B2 | 5/2005 | Wilson et al. ............ 623/1.35 |
| 6,932,837 B2 | 8/2005 | Amplatz et al. ............ 623/1.15 |
| 6,955,687 B2 | 10/2005 | Richter et al. ............ 623/1.35 |
| 6,955,688 B2 | 10/2005 | Wilson et al. ............ 623/1.35 |
| 6,962,602 B2 | 11/2005 | Vardi et al. ............. 623/1.11 |
| 7,018,400 B2 | 3/2006 | Lashinski et al. ............ 623/1.11 |
| 7,056,323 B2 | 6/2006 | Mareiro et al. ............. 606/108 |
| 7,060,091 B2 | 6/2006 | Killion et al. ............ 623/1.15 |
| 2001/0003161 A1 | 6/2001 | Vardi et al. ............. 623/1.11 |
| 2001/0004706 A1 | 6/2001 | Hojeibane ............. 623/1.11 |
| 2001/0004707 A1 | 6/2001 | Dereurne et al. ............ 623/1.16 |
| 2001/0012927 A1 | 8/2001 | Mauch |
| 2001/0016766 A1 | 8/2001 | Vardi et al. ............. 623/1.11 |
| 2001/0016767 A1 | 8/2001 | Wilson et al. |
| 2001/0016768 A1 | 8/2001 | Wilson et al. |
| 2001/0025195 A1 | 9/2001 | Shaolian et al. ............ 623/1.13 |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Dibie |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Boekstegers et al. |
| 2002/0035392 A1 | 3/2002 | Wilson |
| 2002/0042650 A1 | 4/2002 | Vardi et al. |
| 2002/0052648 A1 | 5/2002 | McGuckin et al. |
| 2002/0058990 A1 | 5/2002 | Jang |
| 2002/0072790 A1 | 6/2002 | McGuckin et al. |
| 2002/0107564 A1 | 8/2002 | Cox et al. |
| 2002/0111675 A1 | 8/2002 | Wilson |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 | 12/2002 | Callol et al. |
| 2002/0193872 A1 | 12/2002 | Trout et al. |
| 2002/0193873 A1 | 12/2002 | Brucker et al. |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0028233 A1 | 2/2003 | Vardi et al. .............. 623/1.11 |
| 2003/0050688 A1 | 3/2003 | Fischell et al. |
| 2003/0055378 A1 | 3/2003 | Wang et al. ............. 604/103.07 |
| 2003/0055483 A1 | 3/2003 | Gumm ................ 623/1.11 |
| 2003/0074047 A1 | 4/2003 | Richter |
| 2003/0093109 A1 | 5/2003 | Mauch |
| 2003/0097169 A1 | 5/2003 | Brucker ................ 623/1.11 |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon et al. |
| 2003/0125802 A1 | 7/2003 | Callol et al. |
| 2003/0135259 A1 | 7/2003 | Simso ................ 623/1.12 |
| 2003/0181923 A1 | 9/2003 | Vardi ................. 606/108 |
| 2003/0195606 A1 | 10/2003 | Davidson et al. ........... 623/1.15 |
| 2003/0195609 A1* | 10/2003 | Berenstein et al. ......... 623/1.15 |
| 2004/0006381 A1 | 1/2004 | Sequin et al. ............ 623/1.12 |
| 2004/0015227 A1 | 1/2004 | Vardi et al. |
| 2004/0044396 A1 | 3/2004 | Clerc et al. ............ 623/1.13 |
| 2004/0049259 A1 | 3/2004 | Strecker |
| 2004/0059406 A1 | 3/2004 | Cully et al. ............ 623/1.11 |
| 2004/0072849 A1 | 4/2004 | Schreiber et al. |
| 2004/0088007 A1 | 5/2004 | Eidenschink ............. 607/1 |
| 2004/0117003 A1 | 6/2004 | Ouriel et al. |
| 2004/0133268 A1 | 7/2004 | Davidson et al. |
| 2004/0138732 A1 | 7/2004 | Suhr et al. ............ 623/1.11 |
| 2004/0138737 A1 | 7/2004 | Davidson et al. |
| 2004/0148006 A1 | 7/2004 | Davidson et al. |
| 2004/0172121 A1 | 9/2004 | Eidenschink et al. ........ 623/1.11 |
| 2004/0186560 A1 | 9/2004 | Alt ................... 623/1.35 |
| 2004/0225345 A1 | 11/2004 | Fischell et al. ............ 623/1.11 |
| 2004/0267352 A1 | 12/2004 | Davidson et al. |
| 2005/0004656 A1 | 1/2005 | Das ................... 623/1.16 |
| 2005/0010278 A1 | 1/2005 | Vardi et al. |
| 2005/0015108 A1 | 1/2005 | Williams et al. |
| 2005/0015135 A1 | 1/2005 | Shanley ................ 623/1.11 |
| 2005/0060027 A1 | 3/2005 | Khenansho et al. ......... 623/1.35 |
| 2005/0096726 A1 | 5/2005 | Sequin et al. ............ 623/1.12 |
| 2005/0102021 A1 | 5/2005 | Osborne ............... 623/1.13 |
| 2005/0102023 A1 | 5/2005 | Yadin et al. ............. 623/1.15 |
| 2005/0119731 A1 | 6/2005 | Brucker et al. ............ 623/1.35 |
| 2005/0125076 A1 | 6/2005 | Ginn ................. 623/23.65 |
| 2005/0131526 A1 | 6/2005 | Wong ................. 623/1.15 |
| 2005/0149161 A1 | 7/2005 | Eidenschink et al. ........ 623/1.11 |
| 2005/0154442 A1 | 7/2005 | Eidenschink et al. ........ 623/1.11 |
| 2005/0154444 A1 | 7/2005 | Quadri ................. 623/1.13 |
| 2005/0183259 A1 | 8/2005 | Eidenschink et al. .......... 29/508 |
| 2005/0209673 A1 | 9/2005 | Shaked ................ 623/1.11 |
| 2005/0228483 A1 | 10/2005 | Kaplan et al. ............ 623/1.15 |
| 2006/0036315 A1 | 2/2006 | Yadin et al. ............. 623/1.35 |
| 2006/0041303 A1 | 2/2006 | Israel ................. 623/1.11 |
| 2006/0079956 A1 | 4/2006 | Eigler et al. ............ 623/1.35 |
| 2006/0173528 A1 | 8/2006 | Feld et al. .............. 623/1.15 |
| 2007/0073376 A1 | 3/2007 | Krolik et al. ............ 623/1.11 |
| 2007/0135904 A1 | 6/2007 | Eidenschink |

FOREIGN PATENT DOCUMENTS

| | | |
|---|---|---|
| CA | 2318314 | 7/1999 |
| DE | 9014845.2 | 2/1991 |
| DE | 29701758 | 5/1997 |
| EP | 0479730 | 10/1991 |
| EP | 551179 | 7/1993 |
| EP | 684022 | 11/1995 |
| EP | 0751752 | 1/1997 |
| EP | 804907 | 5/1997 |
| EP | 0783873 | 7/1997 |
| EP | 0479557 | 7/1998 |
| EP | 876805 | 11/1998 |
| EP | 0880949 | 12/1998 |
| EP | 884028 | 12/1998 |
| EP | 891751 | 1/1999 |
| EP | 0895759 | 2/1999 |
| EP | 897698 | 2/1999 |
| EP | 897700 | 2/1999 |
| EP | 904745 | 3/1999 |
| EP | 0937442 | 8/1999 |
| EP | 0347023 | 12/1999 |
| EP | 1031328 | 8/2000 |

| | | |
|---|---|---|
| EP | 1031329 | 8/2000 |
| EP | 1031330 | 8/2000 |
| EP | 0883384 | 12/2000 |
| EP | 0862392 | 8/2001 |
| EP | 1157674 | 11/2001 |
| EP | 0808140 | 12/2001 |
| EP | 1190685 | 3/2002 |
| EP | 646365 | 1/2004 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 95/08965 | 4/1995 |
| WO | WO 95/21592 | 8/1995 |
| WO | WO 96/29955 | 10/1996 |
| WO | WO 96/34580 | 11/1996 |
| WO | WO 96/41592 | 12/1996 |
| WO | 97/07752 | 3/1997 |
| WO | WO 97/09946 | 3/1997 |
| WO | 97/15346 | 5/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | 97/46174 | 12/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | 98/47447 | 10/1998 |
| WO | WO 98/44871 | 10/1998 |
| WO | 98/48879 | 11/1998 |
| WO | WO 98/48733 | 11/1998 |
| WO | WO 98/52497 | 11/1998 |
| WO | 99/03426 | 1/1999 |
| WO | 99/04726 | 2/1999 |
| WO | 99/15109 | 4/1999 |
| WO | WO 99/15103 | 4/1999 |
| WO | WO 99/17680 | 4/1999 |
| WO | 99/24104 | 5/1999 |
| WO | 99/36015 | 7/1999 |
| WO | WO 99/34749 | 7/1999 |
| WO | WO 99/36002 | 7/1999 |
| WO | WO 99/39661 | 8/1999 |
| WO | 99/44539 | 9/1999 |
| WO | 99/56661 | 11/1999 |
| WO | WO 99/58059 | 11/1999 |
| WO | WO 99/65419 | 12/1999 |
| WO | WO 00/00104 | 1/2000 |
| WO | 00/07523 | 2/2000 |
| WO | 00/10489 | 3/2000 |
| WO | 00/16719 | 3/2000 |
| WO | WO 00/12166 | 3/2000 |
| WO | WO 00/13613 | 3/2000 |
| WO | 00/27307 | 5/2000 |
| WO | 00/27463 | 5/2000 |
| WO | 00/28922 | 5/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | WO 00/53122 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | WO 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | WO 02/068012 | 9/2002 |
| WO | WO 02/076333 | 10/2002 |
| WO | WO 02/094336 | 11/2002 |
| WO | 03/007842 | 1/2003 |
| WO | WO 03/055414 | 7/2003 |
| WO | 03/063924 | 8/2003 |
| WO | 2004/026174 | 4/2004 |
| WO | WO 2004/026180 | 4/2004 |
| WO | 2005/009295 | 2/2005 |
| WO | WO 2005/014077 | 2/2005 |
| WO | 2006/028925 | 3/2006 |

OTHER PUBLICATIONS

U.S. Appl. No. 09/614,472, filed Jul. 11, 2000, Davidson et al.
U.S. Appl. No. 09/663,111, filed Sep. 15, 2000, Davidson et al.
Serruys et al., *The New England Journal of Medicine*, vol. 331, No. 8, pp. 489-495 (1994).
Fischmann et al., *The New England Journal of Medicine*, vol. 331, No. 8, pp. 496-501 (1994).
Nakamura et al., *Catheterization & Cardiovascular Diagnosis* 34-353-361 (1995).
Caputo et al., *The American Journal of Cardiology*, vol. 7, pp. 1226-1230 (1996).
Colombo et al., *Catheterization and Cardiovascular Diagnosis*, vol. 30, pp. 327-330 (1993).
Carrie et al., *Catheterization and Cardiovascular Diagnosis*, vol. 37, pp. 311-313 (1996).
Katoh et al., *Catheterization and Cardiovascular Diagnosis*, vol. 40, pp. 400-402 (1997).
Lewis et al., *American Heart Journal*, vol. 127, pp. 1600-1607 (1994).
Dichek, D.A. et al.; *Circulation*, 80:1347-1353 (1989).
Chevalier, B. et al.; *American Journal of Cardiology*, 82: 943-949 (1998).
Yamashita, T. et al.; *Journal of American College of Cardiology*, 35: 1145-1151 (2000).
Satler, S., et al.; *Catheterization and Cardiovascular Interventions*, 50: 411-412 (2000).

* cited by examiner

STENT WITH PROTRUDING BRANCH PORTION FOR BIFURCATED VESSELS

CROSS-REFERENCE TO RELATED APPLICATIONS

The present application is a continuation-in-part of U.S. patent application Ser. No. 10/802,036, filed Mar. 17, 2004 now U.S. Pat. No. 7,341,598, which is a continuation-in-part of U.S. patent application Ser. No. 10/705,247, filed Nov. 12, 2003 now abandoned, which is a continuation-in-part of U.S. patent application Ser. No. 10/644,550, filed Aug. 21, 2003 now U.S. Pat. No. 7,220,275, the entire contents of which are incorporated herein by reference.

FIELD OF THE INVENTION

The present invention relates to the field of medical stents and, more particularly, to a stent for the treatment of lesions and other problems in or near a vessel bifurcation.

BACKGROUND OF THE INVENTION

A stent is an endoprosthesis scaffold or other device that typically is intraluminally placed or implanted within a vein, artery, or other tubular body organ for treating an occlusion, stenosis, aneurysm, collapse, dissection, or weakened, diseased, or abnormally dilated vessel or vessel wall, by expanding the vessel or by reinforcing the vessel wall. In particular, stents are quite commonly implanted into the coronary, cardiac, pulmonary, neurovascular, peripheral vascular, renal, gastrointestinal and reproductive systems, and have been successfully implanted in the urinary tract, the bile duct, the esophagus, the tracheo-bronchial tree and the brain, to reinforce these body organs. Two important current widespread applications for stents are for improving angioplasty results by preventing elastic recoil and remodeling of the vessel wall and for treating dissections in blood vessel walls caused by balloon angioplasty of coronary arteries, as well as peripheral arteries, by pressing together the intimal flaps in the lumen at the site of the dissection. Conventional stents have been used for treating more complex vascular problems, such as lesions at or near bifurcation points in the vascular system, where a secondary artery branches out of a larger, main artery, with limited success rates.

Conventional stent technology is relatively well developed. Conventional stent designs typically feature a straight tubular, single type cellular structure, configuration, or pattern that is repetitive through translation along the longitudinal axis. In many stent designs, the repeating structure, configuration, or pattern has strut and connecting members that impede blood flow at bifurcations. Furthermore, the configuration of struts and connecting members may obstruct the use of post-operative devices to treat a branch vessel in the region of a vessel bifurcation. For example, deployment of a first stent in the main lumen may prevent a physician from inserting a branch stent through the ostium of a branch vessel of a vessel bifurcation in cases where treatment of the main vessel is suboptimal because of displaced diseased tissue (for example, due to plaque shifting or "snow plowing"), occlusion, vessel spasm, dissection with or without intimal flaps, thrombosis, embolism, and/or other vascular diseases. As a result, the physician may choose either to insert a stent into the branch in cases in which such additional treatment may otherwise be unnecessary, or alternatively the physician may elect not to treat, or to "sacrifice", such side lumen. Accordingly, the use of regular stents to treat diseased vessels at or near a vessel bifurcation may create a risk of compromising the benefit of stent usage to the patient after the initial procedure and in future procedures on the main vessel, branch vessels, and/or the bifurcation point.

A regular stent is designed in view of conflicting considerations of coverage versus access. For example, to promote coverage, the cell structure size of the stent may be minimized for optimally supporting a vessel wall, thereby preventing or reducing tissue prolapse. To promote access, the cell size may be maximized for providing accessibility of blood flow and of a potentially future implanted branch stent to branch vessels, thereby preventing "stent jailing", and minimizing the amount of implanted material. Regular stent design has typically compromised one consideration for the other in an attempt to address both. Problems the present inventors observed involving side branch jailing, fear of plaque shifting, total occlusion, and difficulty of the procedure are continuing to drive the present inventors' into the development of novel, non-conventional or special stents, which are easier, safer, and more reliable to use for treating the above-indicated variety of vascular disorders.

Although conventional stents are routinely used in clinical procedures, clinical data shows that these stents are not capable of completely preventing in-stent restenosis (ISR) or restenosis caused by intimal hyperplasia. In-stent restenosis is the reoccurrence of the narrowing or blockage of an artery in the area covered by the stent following stent implantation. Patients treated with coronary stents can suffer from in-stent restenosis.

Many pharmacological attempts have been made to reduce the amount of restenosis caused by intimal hyperplasia. Many of these attempts have dealt with the systemic delivery of drugs via oral or intravascular introduction. However, success with the systemic approach has been limited.

Systemic delivery of drugs is inherently limited since it is difficult to achieve constant drug delivery to the inflicted region and since systemically administered drugs often cycle through concentration peaks and valleys, resulting in time periods of toxicity and ineffectiveness. Therefore, to be effective, anti-restenosis drugs should be delivered in a localized manner.

Although prior art references disclose numerous stents configurations, some of which are coated with one or more drugs, there still remains a need for a stent design that can effectively provide ostial branch support in a vessel bifurcation and effectively act as a delivery vehicle for drugs. Further, there is a need for a bioabsorbable bifurcated stent. This is particularly true in complicated cases, such as lesions located at a bifurcation.

SUMMARY OF THE INVENTION

The present invention is directed to a stent for use in a bifurcated body lumen having a main branch and a side branch. The stent comprises a radially expandable generally tubular stent body having proximal and distal opposing ends with a body wall having a surface extending therebetween. The surface has a geometrical configuration defining a first pattern, and the first pattern has first pattern struts and connectors arranged in a predetermined configuration. The stent also comprises a branch portion comprised of a second pattern, wherein the branch portion is at least partially detachable from the stent body.

In one embodiment of the invention, a bifurcation stent is provided, which comprises a tubular member having an inner diameter and an outer diameter defining a wall therebetween, the wall having a geometrical configuration defining a pattern; and an expandable branch structure formed in the wall of the tubular structure and interrupting the wall pattern, the expandable branch structure having a first ring connected to the tubular member, a second ring connected to the first ring and a third ring connected to the second ring, wherein the expandable branch structure includes a distal portion and a proximal portion, and at least one partial distal ring is connected to the first ring at the distal portion and at least one partial distal ring is connected to the first ring at the proximal portion, and wherein the rings and the partial rings at the proximal and distal portions form a lattice portion, wherein the third ring substantially surrounds and defines a central branch opening, and wherein the expandable branch structure is movable from an unexpanded configuration to an expanded configuration, in the unexpanded configuration the expandable branch structure is disposed along the wall and in the expanded configuration the expandable branch structure extends outwardly from the tubular member.

In another embodiment, the stent's tubular member has a longitudinal axis and the expandable branch structure is disposed substantially perpendicular to the longitudinal axis in the expanded configuration. In a further embodiment, the stent's tubular member comprises a plurality of undulating rings disposed along the longitudinal axis and the undulating rings are connected by connectors. In another embodiment, the first, second and third rings have a common axis disposed substantially perpendicular to the longitudinal axis in the unexpanded configuration.

In a further embodiment of the invention, the branch structure of the stent includes a transition structure. In another embodiment, the transition structure comprises a discontinuous portion. In a further embodiment of the invention, the first ring connects to the discontinuous portion, connects the first ring to a portion of the wall pattern outside the extendible branch structure.

In another embodiment, the first, second and third rings are connected by connectors. In other embodiments, the connectors are generally undulating curvilinear members. In still further embodiments, the connectors are generally straight members. In a further embodiment of the invention, the first, second and third rings are generally continuous undulating curvilinear members and include undulation peaks.

In other embodiments, the stent is comprised of biodegradable material. In further embodiments, the stent is comprised of a material and is coated with a biodegradable material. In further embodiments of the invention, the stent is one of comprised of or coated with a biodegradable material including a drug embedded in the material, whereby upon degradation of the biodegradable material, the drug is controllably released. In another embodiment, the biodegradable material is at least one of polyglycolic acid, polylactic acid, copolymers of polyglycolic acid and polylactic acid, polyorthoesters, polyaminoacids and polyanhydides. In another embodiment, the drug can be embedded in the material in one amount on the expandable branch structure and in another amount on a remainder of the tubular member. In a further embodiment, the first, second and third rings are concentric.

In another embodiment, the first ring is connected to a tubular member by a connector having at least one cell. In one embodiment, the second pattern is configured according to the first pattern having at least one absent connector, and in another embodiment, the second pattern has a plurality of absent connectors. The second pattern may have second pattern struts, and the second pattern struts can be more densely packed than the first pattern struts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the invention may be embodied in practice.

In the drawings.

DESCRIPTION OF THE PREFERRED EMBODIMENTS

Figure 1:
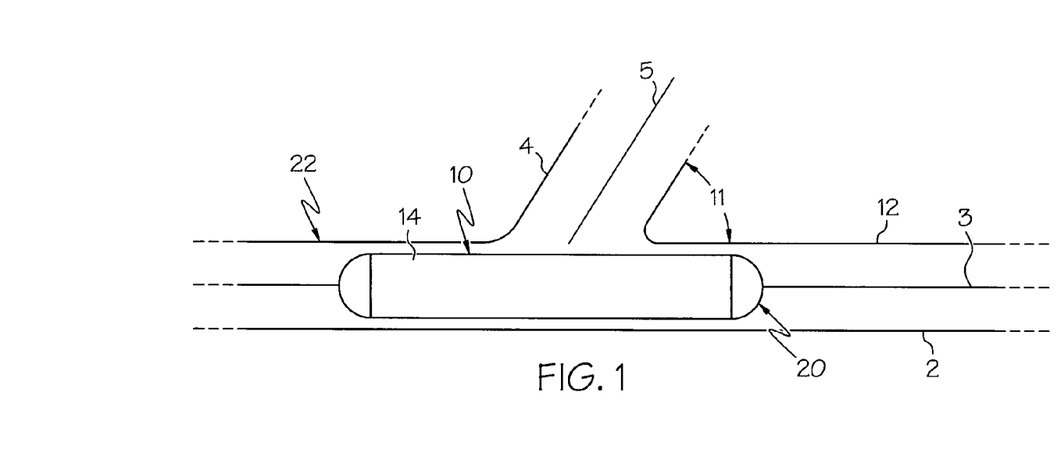
FIG. 1 is an illustration of a blood vessel bifurcation and an unexpanded stent mounted on an exemplary stent delivery system.
Figure 2:
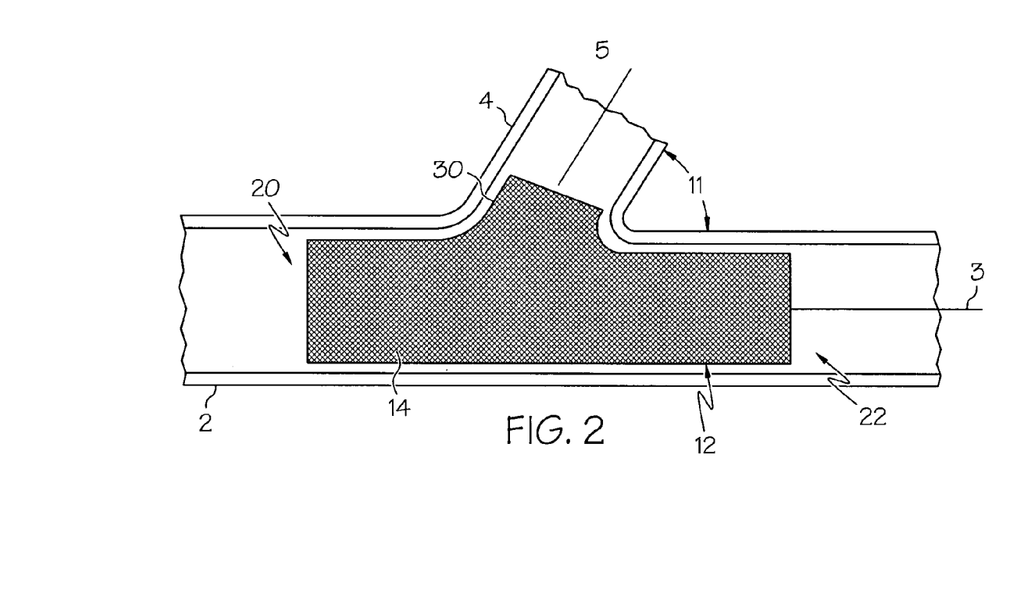
FIG. 2 is an illustration of the stent of FIG. 1 in an expanded condition.

The present invention is directed to a bifurcated stent of the type described in co-pending application Ser. No. 10/802, 036, filed Mar. 17, 2004, the disclosure of which is incorporated by reference. In particular, the present invention relates to stents for placement at vessel bifurcations and that are generally configured to cover a portion of a branch vessel as well as a main vessel. Referring to FIGS. 1 and 2, an exemplary bifurcated blood vessel and bifurcated stent, in accordance with the principles of the invention, are shown. The vessel has a main vessel 2 and a branch vessel 4. Main vessel 2 and branch vessel 4 are disposed at an angle 11, which can be any angle but is shown as an angle of less than 90 degrees by way of example. With reference to FIG. 1, bifurcated stent 10 is shown in an unexpanded condition in FIG. 1. FIG. 2 shows stent 12 in an expanded configuration where branch portion 30 is outwardly deployed from the stent main portion as shown in a representative expanded state in the vasculature.

Stent 12 according to one embodiment of the present invention comprises stent body or wall 14 extending along a longitudinal axis 3 from a proximal end 20 to a distal end 22 and defining a lumen therein. Stent 12 may have a three-dimensional geometrical configuration having variable dimensions (length, width, height, depth, thickness, etc.). In a preferred embodiment, stent body 14 is a generally tubular structure. As defined herein, "tubular" can include an elongate structure that has varied cross-sections and does not require that the cross-section be circular. For example, the cross-section of stent wall 14 may be generally oval. In an alternate embodiment, stent body 14 is generally cylindrical. Also, the stent body 14 may have varied cross-sectional shapes along the longitudinal axis 3 of the stent. For example, the circumferences in the proximal and distal parts of the stent may be different. This may occur, for example, if during stent delivery the delivery system causes the stent to distend. A lumen represents the inner volumetric space bounded by stent body. In a preferred embodiment, stent 12 is radially expandable from an unexpanded state to an expanded state to allow the stent to expand radially and support the main vessel. In the unexpanded state, the stent body defines a lumen having a first volume, and in the expanded state, as illustrated in FIG. 1, the stent body defines a lumen having a second volume larger than the first volume.

Figure 3:
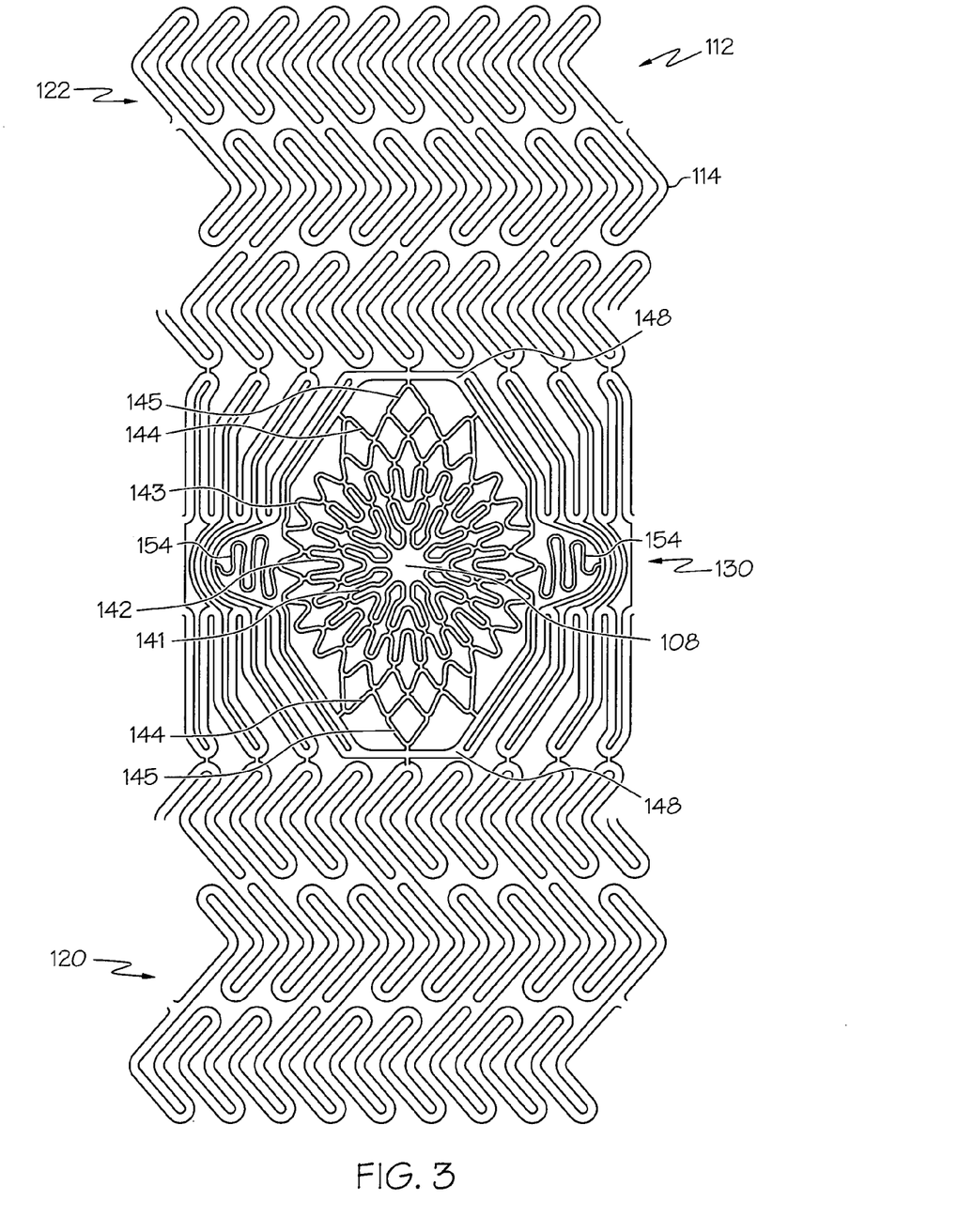
FIG. 3 is a flat view of an embodiment of an unexpanded stent in accordance with the present invention.

FIG. 3 shows stent 112 in an unexpanded state in a flattened elevational view. Stent body 114 has a generally cellular configuration and comprises a generally repeatable series of struts and connectors configured in a predetermined general, overall, or main pattern at the proximal 122 and distal 120 ends of stent 12. Many other strut and connector patterns may be used, and the present pattern is shown for illustration purposes only.

Figure 4:
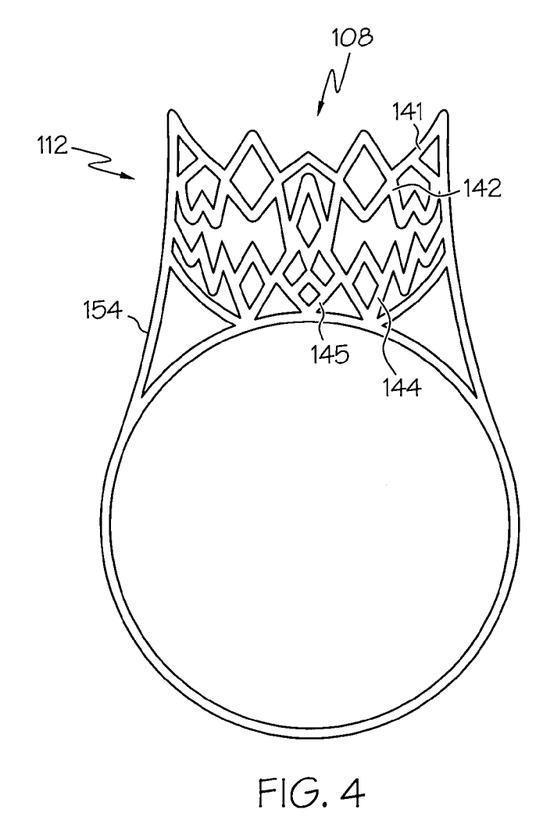
FIG. 4 is an end view of the stent in FIG. 3 in the expanded condition.

Stent 112 further includes a branch portion 130 located at some point along the length of stent 112. Branch portion 130 comprises a section or portion of stent wall 114 that is configured to extend into a branch vessel in a vessel bifurcation as discussed above. In general, branch portion 130 is configured to be movable from an unextended position to an extended position. In the unextended position, branch portion 130 is disposed in the volume defined by the unexpanded stent 112, that is, the branch portion 130 does not protrude radially from stent wall 114 as illustrated in FIG. 1. In the extended position, the branch portion 130 extends outwardly from stent wall 114 and branch portion 130 is extended into the branch vessel as illustrated in FIGS. 2 and 4. Branch portion 130 comprises a stent wall section of stent body 114 that is initially flush, coplanar, or cocylindrical with the remainder of stent body 114 and may extend outwardly with respect to the remainder of stent body 114. This configuration allows for access into a branch vessel, and at the same time allows for circumferential alignment of the stent within the vessel prior to deployment. In other embodiments, multiple branch portions can be incorporated into the stent to permit multiple access to one or more vessels. In a preferred embodiment, branch portion 130 may be positioned in the midsection of stent 112. In alternate embodiments, branch portion 130 may be positioned anywhere along the length of stent 112.

The details of branch portion 130 will be discussed. Branch portion 130 includes three interconnected rings 141, 142 and 143. As shown, rings 141, 142 and 143 are concentric, but could be non-concentric. The inner ring 141 defines undulation petals, prongs, or peaks surrounding a central branch opening 108. Branch opening 108 provides access to the side branch vessel when stent 112 is in the unexpanded condition. In this embodiment, undulation peaks of inner ring 141 are configured differently from the other rings. Rings 142 and 143 are formed, generally, from undulating configurations as shown. The amount and particular configuration of the rings is provided to allow for expansion into the branch. When stent 112 is expanded, as shown in FIG. 4, branch portion 130 is extended into the branch vessel (not shown), causing the expandable rings 141, 142 and 143 to at least partially cover the inner surface of the branch vessel. Thus, in a preferred embodiment, the stent coverage in a portion of the branch vessel includes the full circumference of the inner branch vessel wall. Branch portion 130 may include an auxiliary access opening to provide access to the side branch vessel as described in co-pending application Ser. No. 10/802,036 filed Mar. 17, 2004. Also, in the branch portion 130 may be modified to accommodate markers. Rings 141, 142 and 143 can be interconnected by a plurality of inner connectors as shown.

Outer ring 143 is connected to elliptical transition members 148 as shown and outer connectors 154, which can be generally S-shaped, zigzag-shaped, or wavelike. In this regard, the wavelike shape of distal outer connectors may be deformed to a greater extent and accommodate more expansion than, for example, a straight outer connector design. Outer ring 143 can be connected to partial rings 144 and 145 at the proximal and distal ends of stent 112. Partial ring 144 as shown has four undulations and ring 145 has one. These additional partial rings provide for a lattice configuration at the proximal and distal portion of the branch structure improving coverage thereat. Thus, with this configuration, more coverage is provided when the stent is expanded. Also, with this configuration, varying degrees of coverage or radial support of the side branch vessel wall upon installation into a side branch vessel can be provided. In alternate embodiments, other geometries may be used.

The branch portion 130 protrudes into the branch vessel when the stent is fully expanded. FIG. 4 shows an end view of stent 112 in an expanded configuration. The branch portion upon expansion can extend into the branch vessel in different lengths depending upon the application. The amount of extension may vary in a range between about 0.1-10.0 mm. In one preferred embodiment, the length of extension is 1-3 mm. In another preferred embodiment, the length of extension is approximately 2 mm. In alternative embodiments, the amount of extension into the branch vessel may be variable for different circumferential segments of branch portion 130. As shown in each of the embodiments, the branch portion is approximately 2.5 mm in width and about 2.5-3.0 mm in length. However, the branch portion can be dimensioned to accommodate varying size branch vessels. The branch portion can be formed of any tubular shape to accommodate the branch vessel, including, oval or circular, for example.

Figure 5:
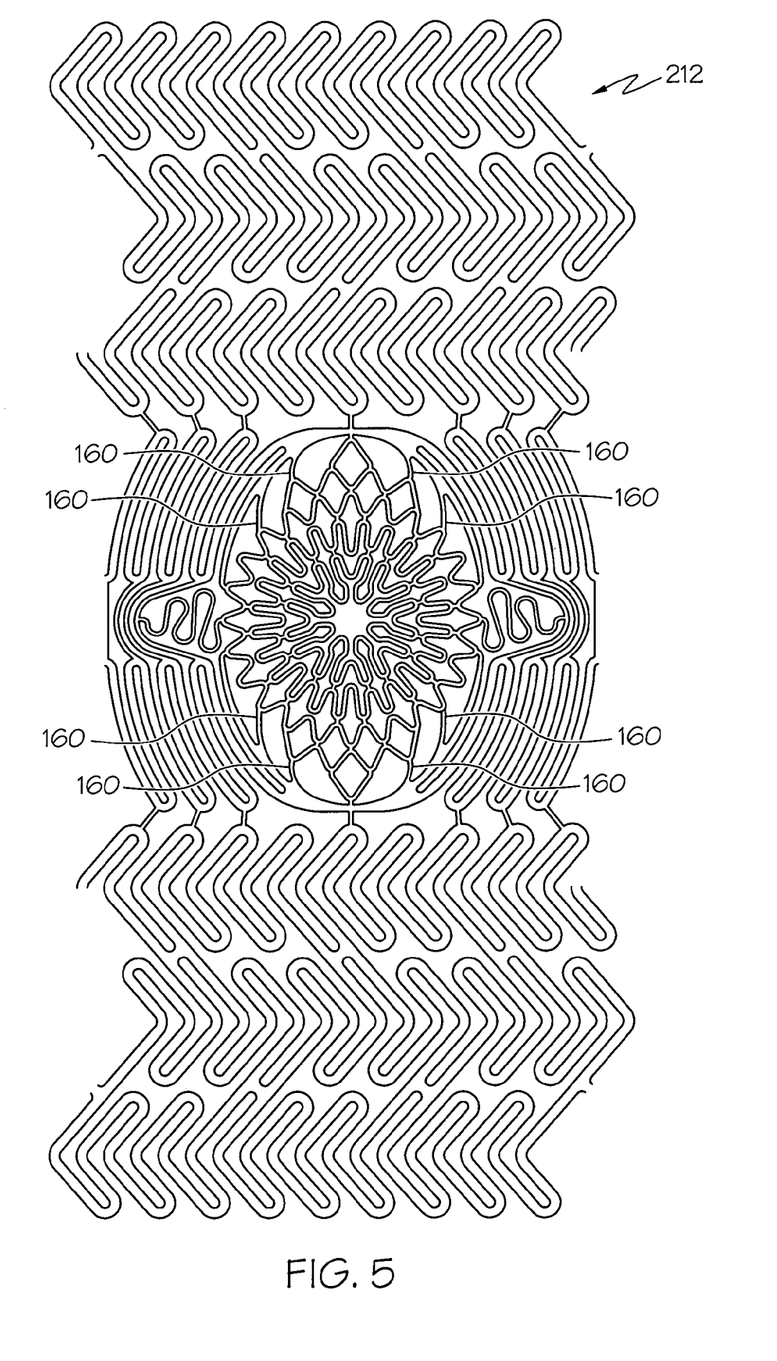
FIG. 5 is a flat view of another embodiment of an unexpanded stent in accordance with the present invention.

FIG. 5 shows an alternate embodiment of the stent shown in FIG. 3. In the embodiment of FIG. 5, stent 212 has substantially the same construction except that additional connectors 160 are provided. Connectors 160 provide additional coverage in the branch vessel.

Figure 6:
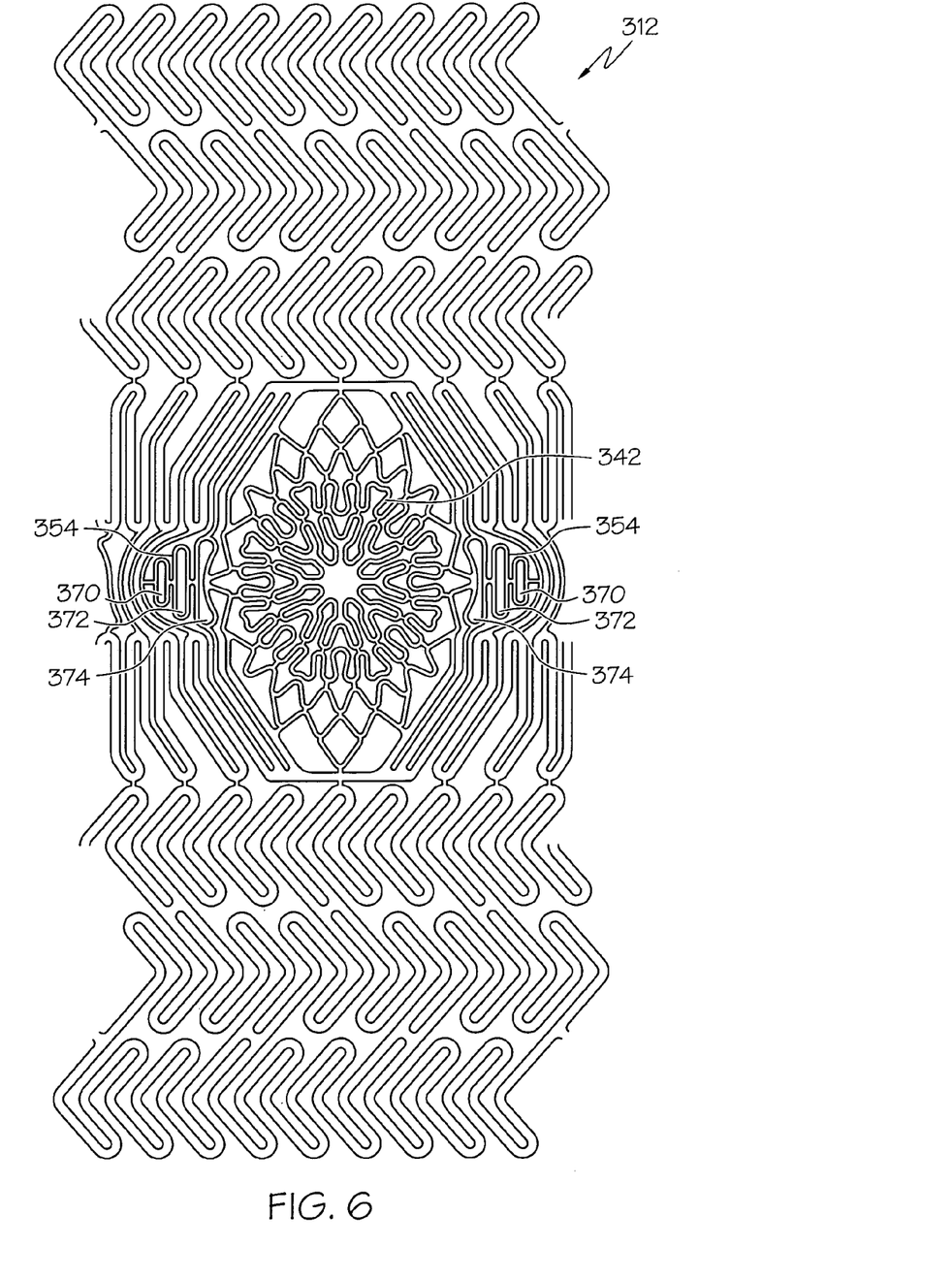
FIG. 6 is a flat view of another embodiment of an unexpanded stent in accordance with the present invention.

FIG. 6 shows an alternate embodiment of the stent shown in FIG. 3. In the embodiment of FIG. 6, stent 312 has substantially the same construction except that connectors 354 are different. Connectors 354 comprise a cellular structure each including three cells 370, 372 and 374. This cellular structure provides improved coverage and radial support. Additionally ring 342 includes a different pattern. Ring 342 has undulations with certain peaks modified to improve coverage.

In general, a wide variety of delivery systems and deployment methods may be used with the aforementioned stent embodiments. For example, a catheter system may be used for insertion and the stent may be balloon expandable or self-expandable, or the stent may be balloon expandable and the branch portion self-expandable, or vice versa. Once the stent is in position in the main vessel and the branch portion is aligned with the side branch the stent can be expanded. If the stent is balloon expandable, the stent may be expanded with a single expansion or multiple expansions. In particular, the stent can be deployed on a stent delivery system having a balloon catheter and side sheath as described, for example, in U.S. Pat. Nos. 6,325,826 and 6,210,429, the entire contents of which are incorporated herein by reference. In one preferred embodiment, a kissing balloon technique may be used, whereby one balloon is configured to expand the stent and the other balloon is configured to extend the branch portion. After the main portion of the stent is expanded in the main vessel, the stent delivery system may be removed and a second balloon may be passed through the side hole in the branch portion and expanded to expand the branch portion of the stent. In an alternate embodiment, the same balloon may be inserted in the main vessel inflated, deflated, retracted and inserted into the branch vessel, and then reinflated to expand the branch portion and cause it to protrude into the branch vessel. Alternatively, the stent can be delivered on two balloons and the main portion and the branch portion can be expanded simultaneously. As needed, the branch portion can be further expanded with another balloon or balloons. Yet another alternative is to use a specially shaped balloon that is capable of expanding the main and branch portions simultaneously. The stent can also be deployed with other types of stent delivery systems. Alternatively, the stent, or portions of the stent, can be made of a self-expanding material, and expansion may be accomplished by using self-expanding materials for the stent or at least the branch portion thereof, such as Nitinol, or by using other memory alloys as are well known in the prior art.

The construction and operation of catheters suitable for the purpose of the present invention are further described in U.S. patent application Ser. No. 09/663,111, filed Sep. 15, 2000, U.S. patent application Ser. No. 10/834,066, filed Apr. 29, 2004, and U.S. patent application Ser. No. 10/893,278, filed Jul. 19, 2004, the disclosures of which are incorporated herein by reference. It should be noted that the catheters taught in the above applications are exemplary, and that other catheters that are suitable with the stents of the subject application are included within the scope of the present application. In alternative embodiments, catheters without balloons may be used. For example, if the stent is comprised of memory alloy such as Nitinol, or is a mechanically self-expanding stent, balloons are not necessarily included on the catheters. Furthermore, any other catheter, including ones that are not disclosed herein, may be used to position stents according to the present invention.

Figure 7:
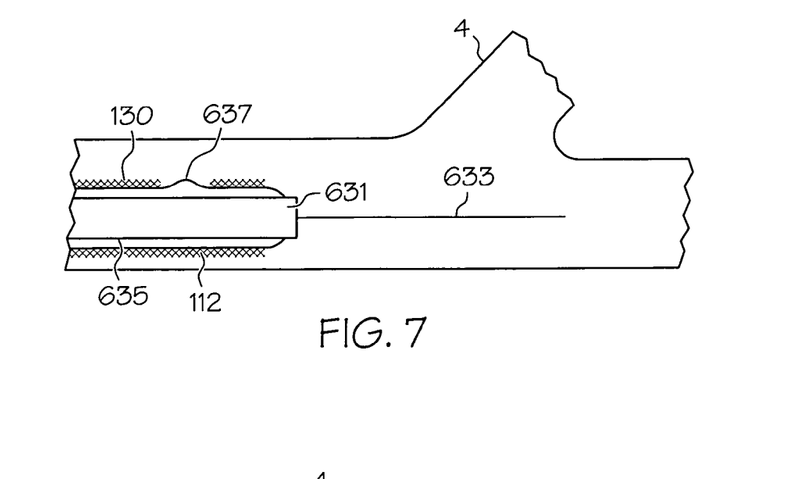
FIGS. 7-9 are illustrations of the steps for a method of inserting a stent of the present invention according to one embodiment of the invention.
Figure 8:
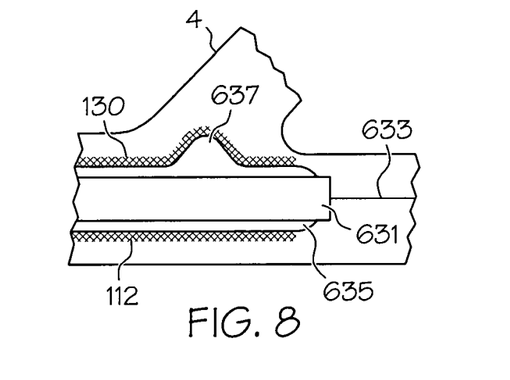
Figure 9:
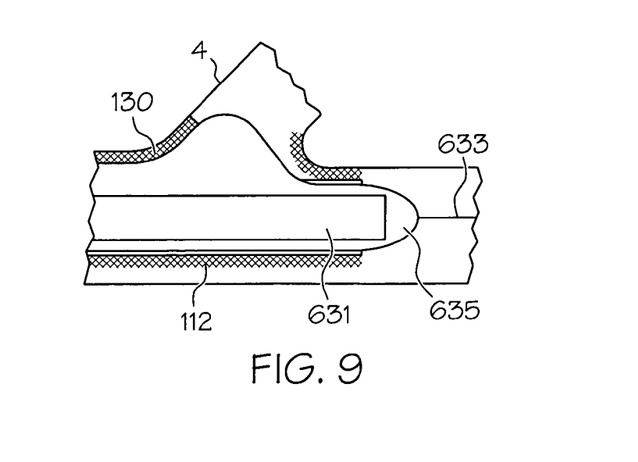

Referring now to FIGS. 7-9, illustrations of the steps of a method for employing a stent of the present invention is shown. By way of example, the method is depicted utilizing stent 112. The depicted method may be accomplished using a catheter system having a main catheter 631 including a herniated balloon 635 (FIG. 9). In particular, the stent can be deployed on a stent delivery system having a herniated balloon as described, for example, in U.S. patent application Ser. No. 10/834,066, the entire contents of which are incorporated herein by reference. As shown in FIG. 7, the catheter 631 includes a balloon 635 that has a protruding portion 637 that, upon expansion, protrudes outwardly from the cylindrical outer surface of the balloon causing the branch portion 130 to be extended into branch vessel 4.

Referring again to FIGS. 7-9, protruding portion 637 may be configured to fit directly into an opening in the stent. As shown in FIG. 7, catheter 631 is advanced over a guidewire 633 and positioned proximal to the bifurcation. As shown in FIG. 8, the catheter is advanced until the protruding portion 637 of the balloon is positioned at the bifurcation. In one embodiment, protruding portion 637 protrudes outwardly from catheter 631 enough so that it actually comes into contact with the bifurcation, thus providing a method of alignment with the branch vessel 4. Finally, as shown in FIG. 9, balloon 635 is expanded, which simultaneously causes the stent to expand and branch portion 130 to be pushed toward the branch vessel 4. Upon inflation of the balloon, the herniated portion 637 expands and extends through the branch portion 130 toward the side branch to open the entrance of the occluded side branch artery.

In an alternative method, the stent can be delivered using a herniated balloon and a dual lumen delivery system. This system can include a main catheter defining a first lumen with concentric guidewire lumen and balloon inflation lumen, a herniated balloon, as described above, on the main catheter, a side sheath with a guidewire lumen, and a stent. The stent is crimped over the main catheter, balloon and side sheath with the side sheath exiting the stent through a branch opening or side hole. The distal end of the side sheath is used for aligning the stent branch opening with the branch vessel 4.

The appendage or herniation may be located on a second catheter or side sheath of the delivery system, such as the system or as a bifurcated or split herniated balloon as described in U.S. patent application Ser. No. 10/834,066, and U.S. patent application Ser. No. 10/893,278, which are incorporated herein by reference.

One particular application for the use of a stent with a branch portion such as the one described above is for localized drug delivery. Restenosis, including in-stent restenosis, is a common problem associated with medical procedures involving the vasculature. Pharmaceutical agents have been found to be helpful in treating and/or preventing restenosis, and these are best delivered locally to the site of potential or actual restenosis, rather than systemically. Stents according to the present invention can also be used as vehicles for localized delivery of other drugs.

The stent in accordance with the invention can be made of any material or combination of materials including stainless steel and/or biodegradable materials. For example, the stent can be made of solely biodegradable material or a conventional material coated with biodegradable material. A drug, drug compound or pharmaceutical agent can be used, for example, by embedding it in the biodegradable material. This can accomplish, among other things, time release. In particular, upon degradation of the stent or coating, the drug is released in a controllable preprogrammed fashion. Biodegradable polymers that are usable in the context of the present invention include, without limitation, poly(L-lactic add), polycaprolactone, poly(lactide-co-glycolide), poly(hydroxybutyrate), poly(hydroxybutyrate-co-valerate), polydioxanone, polyorthoester, polyanhydride, poly(glycolic acid), poly(lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen, hyaluronic acid copolymers are also contemplated.

The present invention also provides kits comprising a stent or stents according to the present invention. In addition to a stent or stents, a kit according to the present invention may include, for example, delivery catheter(s), balloon(s), and/or instructions for use. In kits according to the present invention, the stent(s) may be mounted in or on a balloon or catheter. Alternatively, the stent(s) may be separate from the balloon or catheter and may be mounted therein or thereon prior to use.

While the invention has been described in conjunction with specific embodiments and examples thereof, it is evident that many alternatives, modifications and variations will be apparent to those skilled in the art upon reading the present disclosure. One or more features of one embodiment can be used in other embodiments. Accordingly, it is intended to embrace all such alternatives, modifications and variations that fall within the spirit and broad scope of the appended claims.

What is claimed is:

1. A bifurcation stent, comprising:
    a tubular member having an inner diameter and an outer diameter defining a wall therebetween, the wall having a geometrical configuration defining a pattern; and
    an expandable branch structure formed in the wall of the tubular structure and interrupting the wall pattern, the expandable branch structure being connected to the tubular member at a plurality of locations, the expandable branch structure having a first ring connected to the tubular member, a second ring connected to the first ring and a third ring connected to the second ring, wherein the expandable branch structure includes a distal portion and a proximal portion, and at least one partial distal ring is connected to the first ring at the distal portion and at least one partial proximal ring is connected to the first ring at the proximal portion, and wherein the rings and the partial rings at the proximal and distal portions form a lattice portion, wherein the third ring substantially surrounds and defines a central branch opening, and wherein the expandable branch structure is movable from an unexpanded configuration to an expanded configuration, in the unexpanded configuration the expandable branch structure is disposed along the wall and in the expanded configuration the expandable branch structure extends outwardly from the tubular member.

2. The stent according to claim 1, wherein the tubular member has a longitudinal axis and the expandable branch structure is disposed substantially perpendicular to the longitudinal axis in the expanded configuration.

3. The stent according to claim 1, wherein the tubular member comprises a plurality of undulating rings disposed along the longitudinal axis and the undulating rings are connected by connectors.

4. The stent according to claim 1, wherein the first, second and third rings have a common axis disposed substantially perpendicular to the longitudinal axis in the unexpanded configuration.

5. The stent according to claim 1, wherein the branch structure includes a transition structure.

6. The stent according to claim 5, wherein the transition structure comprises a discontinuous portion.

7. The stent according to claim 6, wherein the first ring connects to the discontinuous portion, connects the first ring to a portion of the wall pattern outside the extendible branch structure.

8. The stent according to claim 5, wherein the first, second and third rings are connected by connectors.

9. The stent according to claim 8, wherein the connectors are generally undulating curvilinear members.

10. The stent according to claim 8, wherein the connectors are generally straight members.

11. The stent according to claim 3, wherein the first, second and third rings are generally continuous undulating curvilinear members and include undulation peaks.

12. The stent according to claim 1, wherein the stent is comprised of biodegradable material.

13. The stent according to claim 1, wherein the stent is comprised of a material and is coated with a biodegradable material.

14. The stent according to claim 1, wherein the stent is one of comprised of or coated with a biodegradable material including a drug embedded in the material, whereby upon degradation of the biodegradable material, the drug is controllably released.

15. The stent according to claim 12, wherein the biodegradable material is at least one of polyglycolic acid, polylactic acid, copolymers of polyglycolic acid and polylactic acid, polyorthoesters, polyaminoacids and polyanhydides.

16. The stent according to claim 13, wherein the biodegradable material is at least one of polyglycolic acid, polylactic acid, copolymers of polyglycolic acid and polylactic acid, polyorthoesters, polyaminoacids and polyanhydides.

17. The stent according to claim 14, wherein the drug can be embedded in the material in one amount on the expandable branch structure and in another amount on a remainder of the tubular member.

18. The stent according to claim 1, wherein the first, second and third rings are concentric.

19. The stent according to claim 1, wherein the first ring is connected to a tubular member by a connector having at least one cell.

* * * * *